United States Patent
Kawabe et al.

(12)

(10) Patent No.: US 6,936,445 B2
(45) Date of Patent: Aug. 30, 2005

(54) ENZYME PREPARATION AND METHOD OF USING THE SAME

(75) Inventors: Tomoyasu Kawabe, Nishinomiya (JP); Masashi Kamitamari, Toyonaka (JP)

(73) Assignee: Sumitomo Chemical Company, Limited, Osaka (JP)

( * ) Notice: Subject to any disclaimer, the term of this patent is extended or adjusted under 35 U.S.C. 154(b) by 469 days.

(21) Appl. No.: 10/231,478

(22) Filed: Aug. 30, 2002

(65) Prior Publication Data

US 2003/0124683 A1 Jul. 3, 2003

(30) Foreign Application Priority Data

Sep. 3, 2001 (JP) ........................................ 2001-265495

(51) Int. Cl.$^7$ ......................... C12N 15/55; C12N 11/08; C12N 9/16; C12P 17/10; C12P 13/04
(52) U.S. Cl. ......................... 435/121; 435/180; 435/196
(58) Field of Search ................................. 435/121, 180, 435/196

(56) References Cited

U.S. PATENT DOCUMENTS

| | | | |
|---|---|---|---|
| 5,166,064 A | | 11/1992 | Usui et al. |
| 5,292,649 A | | 3/1994 | Kosugi et al. |
| 5,839,258 A | | 11/1998 | Takayanagi et al. |
| 2002/0164727 A1 | * | 11/2002 | Kishimoto et al. .......... 435/121 |
| 2002/0173013 A1 | * | 11/2002 | Kishimoto et al. .......... 435/121 |

FOREIGN PATENT DOCUMENTS

| | | |
|---|---|---|
| EP | 1 057 894 A2 | 12/2000 |
| JP | 6-16718 | 3/1994 |

* cited by examiner

*Primary Examiner*—Herbert J. Lilling
(74) *Attorney, Agent, or Firm*—Fitch Even Tabin & Flannery

(57) ABSTRACT

There is disclosed are an enzyme preparation characterized by a polymer carrier having fine pores with average radius of 200–500 Å and the enzyme is capable of converting an N-substituted cyclic imino ester into an (S)-N-substituted cyclic imino acid, thereby an (S)-N-substituted cyclic imino acid is preferentially produced, and has an amino acid sequence as set forth in SEQ ID NO: 1 or the like.

10 Claims, 1 Drawing Sheet

SEQUENCE LISTING

<160> NUMBER OF SEQ ID NOS: 2

<210> SEQ ID NO 1
<211> LENGTH: 255
<212> TYPE: PRT
<213> ORGANISM: Aspergillus flavus

<400> SEQUENCE: 1

Met His Leu Pro Ile Lys Thr Leu Phe Val Ser Leu Leu Gly Ala Ser
1               5                   10                  15

Val Leu Ala Arg Pro Leu Pro Asn Asp Ala Leu Val Glu Arg Asn Ala
            20                  25                  30

Pro Leu Asn Glu Phe Leu Ser Val Leu Ser His Leu Pro Ala Ile
        35                  40                  45

Asn Gly Ser Ile Thr Ala Val Ser Gly Leu Ile Thr Asp Phe Asp Gln
    50                  55                  60

Leu Leu Ala Asp Ile Thr Gly Ala Gln Thr Thr Leu Asn Gly Phe Thr
65                  70                  75                  80

Gly Ala Cys Thr Asp Tyr Thr Val Leu Phe Ala Arg Gly Thr Ser Glu
                85                  90                  95

Pro Gly Asn Val Gly Val Leu Val Gly Pro Pro Leu Ala Glu Ala Phe
            100                 105                 110

Glu Gly Ala Val Gly Ala Ser Ala Leu Ser Phe Gln Gly Val Asn Gly
        115                 120                 125

Tyr Ser Ala Ser Val Glu Gly Tyr Leu Ala Gly Glu Ala Ala Gly
    130                 135                 140

Ser Lys Ala Met Ala Ser Gln Ala Ser Asp Ile Leu Ser Lys Cys Pro
145                 150                 155                 160

Asp Thr Lys Leu Val Met Ser Gly Tyr Ser Gln Gly Cys Gln Ile Val
                165                 170                 175

His Asn Ala Val Glu Gln Leu Pro Ala Glu His Ala Ser Lys Ile Ser
            180                 185                 190

Ser Val Leu Leu Phe Gly Asp Pro Tyr Lys Gly Lys Ala Leu Pro Asn
        195                 200                 205

Val Asp Ala Ser Arg Val His Thr Val Cys His Ala Gly Asp Thr Ile
    210                 215                 220

Cys Glu Asn Ser Val Ile Ile Leu Pro Ala His Leu Thr Tyr Ala Val
225                 230                 235                 240

Asp Val Ala Ser Ala Ala Asp Phe Ala Val Ala Ala Lys Asn
                245                 250                 255

<210> SEQ ID NO 2
<211> LENGTH: 768
<212> TYPE: DNA
<213> ORGANISM: Aspergillus flavus
<220> FEATURE:
<221> NAME/KEY: CDS
<222> LOCATION: (1)..(765)

<400> SEQUENCE: 2 atg cat ctt cct atc aag act ctc ttt gtc tct ctc ctc gga gcc agc        48
Met His Leu Pro Ile Lys Thr Leu Phe Val Ser Leu Leu Gly Ala Ser
1               5                   10                  15 gtt ctc gca cgc cct ctt ccc aat gat gct ctc gtt gag aga aac gct        96
Val Leu Ala Arg Pro Leu Pro Asn Asp Ala Leu Val Glu Arg Asn Ala
            20                  25                  30

-continued

```
ccc cta aac gag ttc ctc agc gtc ctt ctg tct cat ttg cct gcc att       144
Pro Leu Asn Glu Phe Leu Ser Val Leu Leu Ser His Leu Pro Ala Ile
        35                  40                  45 aac ggc tct atc act gcg gtg tcg ggt ctg atc acc gat ttt gat caa       192
Asn Gly Ser Ile Thr Ala Val Ser Gly Leu Ile Thr Asp Phe Asp Gln
 50                  55                  60 ttg ctt gct gac atc acc ggt gct caa aca acc ctg aat gga ttt act       240
Leu Leu Ala Asp Ile Thr Gly Ala Gln Thr Thr Leu Asn Gly Phe Thr
 65                  70                  75                  80 ggt gcc tgc acg gat tac acc gtt ctc ttc gcc cgc gga acc agt gag       288
Gly Ala Cys Thr Asp Tyr Thr Val Leu Phe Ala Arg Gly Thr Ser Glu
                 85                  90                  95 ccc gga aac gtt ggt gtc ctc gtc gga cct cct ctt gct gag gcg ttt       336
Pro Gly Asn Val Gly Val Leu Val Gly Pro Pro Leu Ala Glu Ala Phe
             100                 105                 110 gag gga gcc gtc ggt gcg tcc gcc ttg agc ttc cag ggt gtc aac ggc       384
Glu Gly Ala Val Gly Ala Ser Ala Leu Ser Phe Gln Gly Val Asn Gly
         115                 120                 125 tat tct gca tct gtc gag gga tat ttg gct gga ggt gaa gcc gct ggc       432
Tyr Ser Ala Ser Val Glu Gly Tyr Leu Ala Gly Gly Glu Ala Ala Gly
130                 135                 140 agc aag gca atg gca tct cag gcc agc gac att ctc tcc aag tgt ccc       480
Ser Lys Ala Met Ala Ser Gln Ala Ser Asp Ile Leu Ser Lys Cys Pro
145                 150                 155                 160 gac acc aag ctt gtc atg agt ggc tat tcc cag ggc tgc cag att gtt       528
Asp Thr Lys Leu Val Met Ser Gly Tyr Ser Gln Gly Cys Gln Ile Val
                 165                 170                 175 cac aat gcc gtt gag caa ctt cct gcg gaa cac gca agc aag atc agc       576
His Asn Ala Val Glu Gln Leu Pro Ala Glu His Ala Ser Lys Ile Ser
             180                 185                 190 agc gtc ctc ctt ttc gga gac cca tac aag ggc aag gct ctc ccc aac       624
Ser Val Leu Leu Phe Gly Asp Pro Tyr Lys Gly Lys Ala Leu Pro Asn
         195                 200                 205 gtt gat gct tcc cgc gtc cac act gtg tgc cac gct gga gac act att       672
Val Asp Ala Ser Arg Val His Thr Val Cys His Ala Gly Asp Thr Ile
210                 215                 220 tgc gag aac agc gtt att att ctg ccc gct cac ttg acc tac gct gtt       720
Cys Glu Asn Ser Val Ile Ile Leu Pro Ala His Leu Thr Tyr Ala Val
225                 230                 235                 240 gat gtg gct tct gcg gct gac ttc gct gtt gcg gct gca aag aac taa       768
Asp Val Ala Ser Ala Ala Asp Phe Ala Val Ala Ala Lys Asn
                 245                 250                 255
```

ENZYME PREPARATION AND METHOD OF USING THE SAME

BACKGROUND OF THE INVENTION

The present invention relates to an enzyme preparation, which enzyme is an enzyme having an ability to asymmetrically hydrolyze an N-benzylazetidine-2-carboxylic acid ester to preferentially produce an (S)—N-benzylazetidine-2-carboxylic acid, which is a useful production intermediate of pharmaceuticals, and a process for producing (S)-N-substituted cyclic imino acid using said enzyme preparation.

JP-A-2001-46084 discloses a process for producing an (S)-N-substituted cyclic imino acid by asymmetrically hydrolyzing a racemic compound thereof with a separated aqueous enzyme solution, however, said process was not always satisfactory for industrial scale of production in that it was difficult to isolate the produced imino acid from the resulting aqueous phase of the reaction mixture containing the same and amino acids derived from the enzyme solution after completion of the reaction.

SUMMARY OF THE INVENTION

According to the present invention, separation of the desired product is readily accomplished by using the enzyme preparation of the present invention.

The present invention provides:

1. an enzyme preparation(hereinafter referred to as "the present enzyme preparation"), comprising:

(i) a styrene-divinylbenzene copolymer having fine pores with an average radius of 200–500 Å, (ii) an enzyme capable of asymmetrically hydrolyzing N-substituted C3–C4 cyclic imino-2-carboxylic acid ester to preferentially produce an (S)-N-substituted C3–C4 cyclic imino-2-carboxylic acid, and wherein said enzyme comprises any one of the following amino acid sequences (a) to (f):

(a) an amino acid sequence as set forth in SEQ ID NO: 1;

(b) an amino acid sequence as represented by the sequence corresponding to 35th to 255th amino acid in SEQ ID NO: 1;

(c) an amino acid sequence as represented by the sequence corresponding to 79th to 255th amino acid in SEQ ID NO: 1;

(d) an amino acid sequence that is encoded by a DNA, wherein 1) said DNA is a DNA that hybridizes with a DNA consisting of a nucleotide sequence coding for the amino acid sequence as set forth in SEQ ID NO: 1 at a high ion concentration of 6×SSC (900 mM NaCl, 90 mM sodium citrate) at a temperature of 65° C., and 2) the resulting hybrid is maintained after being incubated under a low ion concentration of 0.1×SSC (15 mM NaCl, 1.5 mM sodium citrate) at a temperature of 65° C. for 30 minutes;

(e) an amino acid sequence that has sequence identity with the amino acid sequence as set forth in SEQ ID NO: 1 of 70% or greater; or (f) an amino acid sequence encoded by a nucleotide sequence having the restriction sites (NcoI, HinFI, FbaI, FbaI, MunI, AccII/SacII, BcnI, AvaII, HincII, HaeIII, HindIII and AccII in said order) as shown in FIG. 1; and 2. a process for producing an (S)-N-substituted cyclic imino acid of formula (2):

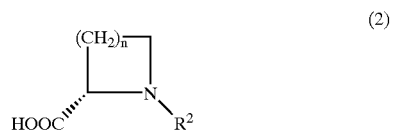

wherein $R^2$ represents
    an aralkyl group having 7 to 19 carbon atoms,
    an alkylcarbonyl group having 2 to 5 carbon atoms,
    an arylcarbonyl group having 7 to 13 carbon atoms,
    an alkyloxycarbonyl group having 2 to 9 carbon atoms,
    an aralkyloxycarbonyl group having 8 to 10 carbon atoms,
    an alkenyloxycarbonyl group having 4 to 9 carbon atoms,
    an aryloxycarbonyl group having 7 to 13 carbon atoms,
    an alkyl group having 1 to 8 carbon atoms,
    an alkenyl group having 2 to 8 carbon atoms,
    an aryl group having 6 to 12 carbon atoms, or
    an arylsulfonyl group having 6 to 12 carbon atoms,
    wherein said aralkyl, arylcarbonyl, aralkyloxycarbonyl, aryloxycarbonyl, aryl or arylsulfonyl group may be substituted on the aromatic ring thereof with at least one group selected from
    an alkyl group having 1 to 8 carbon atoms,
    an alkoxy group having 1 to 8 carbon atoms,
    a halogen atom and a nitro group, and
    wherein said alkylcarbonyl, alkyloxycarbonyl or alkyl group may be substituted with at least one group selected from
    an alkoxy group having 1 to 8 carbon atoms,
    a halogen atom and a nitro group; and
    n represents 1 or 2,
    which process (hereinafter referred to as "the present process") comprises subjecting an N-substituted cyclic imino ester of formula (1):

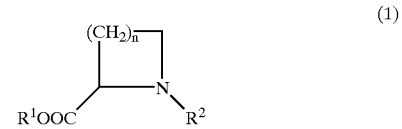

to a reaction with the enzyme preparation as defined above, wherein in formula (1) $R^1$ represents
    an alkyl group having 1 to 8 carbon atoms,
    an aralkyl group having 7 to 19 carbon atoms,
    an alkenyl group having 2 to 5 carbon atoms or
    an aryl group having 6 to 12 carbon atoms,
    and wherein said alkyl group may be substituted with at least one group selected from
    an alkoxy group having 1 to 8 carbon atoms,
    a halogen atom and a nitro group, and
wherein said aralkyl or aryl group may be substituted on the aromatic ring thereof with at least one selected from
    an alkyl group having 1 to 8 carbon atoms,
    an alkoxy group having 1 to 8 carbon atoms,
    a halogen atom and a nitro group; and
    $R^2$ and n have the same meaning as defined above.

Figure 1:
FIG. 1 shows a restriction sites of the nucleotide sequence (DNA), depicted by a bold line, that codes for the amino acid sequence of the present invention, wherein restriction sites: NcoI, HinFI, FbaI, FbaI, MunI, AccII/SacII, BcnI, AvaII, HincII, HaeIII, HindIII and AccII align in said order.

DETAILED DESCRIPTION OF THE INVENTION $R^1$ and $R^2$ groups and substituent groups which may be present thereon in formula (1) and (2) will be explained first.

Examples of the alkyl group having 1 to 8 carbon atoms include, for example, a methyl, ethyl, n-propyl, i-propyl, n-butyl, i-butyl, s-butyl, t-butyl, n-pentyl, neo-pentyl, n-hexyl, n-heptyl, and n-octyl groups.

Examples of the aralkyl group having 7 to 19 carbon atoms include, for example, a benzyl group, a phenethyl group, a naphthylmethyl group, a trityl group and the like.

Examples of the an alkenyl group having 2 to 5 carbon atoms include, for example, a vinyl group, a propenyl group, a butenyl group, a pentenyl group, and the like.

Examples of the aryl group having 6 to 12 carbon atoms include, for example, a phenyl group, a naphthyl group, a biphenyl group and the like.

Examples of the alkoxy group having 1 to 8 carbon atoms include, for example, a methoxy, ethoxy, n-propoxy, i-propyl, n-butoxyy, i-butoxy, s-butoxy, t-butoxy, n-pentyloxy, neo-pentyloxy, n-hexyloxy, n-heptyloxy, and n-octyloxy groups.

Examples of the halogen atom include a fluorine atom, a chlorine atom, a bromine atom and an iodine atom.

Examples of the alkylcarbonyl group having 2 to 5 carbon atoms, for example, a methylcarbonyl group, an ethylcarbonyl group, a propylcarbonyl group, a butylcarbonyl group and the like.

Examples of the arylcarbonyl group having 7 to 13 carbon atoms include, a phenylcarbonyl group, a naphthylcarbonyl group, a biphenylcarbonyl group and the like.

Examples of the alkyloxycarbonyl group having 2 to 9 carbon atoms include, for example, a methoxycarbonyl group, an ethoxycarbonyl group, a propoxycarbonyl group, a butoxycarbonyl group, a pentyoxycarbonyl group, a hexyloxycarbonyl group, a heptyloxycarbonyl group, a octyloxycarbonyl group and the like.

Examples of the aralkyloxycarbonyl group having 8 to 10 carbon atoms include, for example, a benzyloxycarbonyl group, a phenethyloxycarbonyl group, a phenylpropylcarbonyl group.

Examples of the alkenyloxycarbonyl group having 4 to 9 carbon atoms include, for example, a propenyloxycarbonyl group, a butenyloxycarbonyl group, a pentenyloxycarbonyl group, a heptenyloxycarbonyl group, a octenyloxycarbonyl group and the like.

Examples of the aryloxycarbonyl group having 7 to 13 carbon atoms include, for example, a phenyloxycarbonyl group, a naphthyloxycarbonyl group, biphenyloxycarbonyl group and the like.

Examples of the alkenyl group having 2 to 8 carbon atoms, a vinyl group, a propenyl group, a butenyl group, a pentenyl group, a hexeneyl group, a heptenyl group, a octenyl group and the like.

Examples of the arylsulfonyl group having 6 to 12 carbon atoms include, for example, a phenylsulfonyl group, a naphthylsulfonyl group, a biphenylsulfonyl group and the like.

Examples of the cyclic imino ester, wherein n representing 1 or 2, include, for example azetidine carboxylic acid, and pyrrolidine carboxylic acid.

$R^1$ preferably represents C1–C4 alkyl group and more preferably a methyl group and an ethyl group. $R^2$ preferably represents a benzyl group.

Specific examples of the N-substituted C3–C4 cyclic imino-2-carboxylic acid of formula (1) include following compounds:

methyl N-benzylazetidine-2-caroxylate,
methyl N-p-chlorobenzylazetidine-2-carboxylate,
methyl N-[(S)-phenylethyl]azetidine-2-carboxylate,
methyl N-[(R)-phenylethyl]azetidine-2-carboxylate,
methyl N-β-phenylethylazetidine-2-carboxylate,
methyl N-phenylpropylazetidine-2-carboxylate,
methyl N-benzhydrylazetidine-2-carboxylate,
methyl N-triphenylmethylazetidine-2-carboxylate,
methyl N-acetylazetidine-2-carboxylate,
methyl N-chloroacetylazetidine-2-carboxylate,
methyl N-trifluoroacetylazetidine-2-carboxylate,
methyl N-benzoylazetidine-2-carboxylate,
methyl N-p-phenylbenzoylazetidine-2-carboxylate,
methyl N-t-butoxycarbonylazetidine-2-carboxylate,
methyl N-trichloroethyloxycarbonylazetidine-2-carboxylate,
methyl N-benzyloxycarbonylazetidine-2-carboxylate,
methyl N-p-nitrobenzyloxycarbonylazetidine-2-carboxylate,
methyl N-2-phenylethyloxycarbonylazetidine-2-carboxylate,
methyl N-allyloxycarbonylazetidine-2-carboxylate,
methyl N-2,4,6-tri-t-butylphenyloxycarbonyl-azetidine-2-carboxylate,
methyl N-methylazetidine-2-carboxylate,
methyl N-ethylazetidine-2-carboxylate,
methyl N-n-propylazetidine-2-carboxylate,
methyl N-i-propylazetidine-2-carboxylate,
methyl N-n-butylazetidine-2-carboxylate,
methyl N-i-butylazetidine-2-carboxylate,
methyl N-sec-butylazetidine-2-carboxylate,
methyl N-t-butylazetidine-2-carboxylate,
methyl N-allylazetidine-2-carboxylate,
methyl N-phenylazetidine-2-carboxylate,
methyl N-p-toluenesulfonylazetidine-2-carboxylate,
methyl N-benzenesulfonylazetidine-2-carboxylate,
methyl N-methoxybenzenesulfonylazetidine-2-carboxylate, and
methyl N-nitrobenzenesulfonylazetidine-2-carboxylate.

Further examples of the compound of formula (1) include those compounds having ethyl, n-propyl, isopropyl, n-butyl, isobutyl, sec-butyl, t-butyl, benzyl, (S)-α-phenethyl, (R)-α-phenethyl, β-phenylethyl, phenylpropyl, benzhydryl, triphenylmethyl, ally, phenyl, or naphthyl in place of methyl residue in the ester compounds exemplified above. Examples of the N-substituted C3–C4 cyclic imino-2-carboxylic acid of formula (1) include those compounds having a pyrrolidine-2-carboxylate in place of the azetidine-2-carboxylate in the exemplified compounds above.

The compound of formula (1) is typically a racemic compound and may also include a composition containing (S)-N-substituted C3–C4 cyclic imino acid ester of formula (2) and an antipode ester thereof.

Examples of the (S)-N-substituted cyclic imino acid ester of formula (2) include (S)-N-substituted-azetidine-2-carboxylic acid or (S)-N-substituted-pyrrolidine-2-carboxylic acid having various N-substituents as exemplified above.

The amino acid sequences defined under (a) to (f) will be explained next.

Examples of "the amino acid sequence consisting of a part of the amino acid sequence as set forth in SEQ ID NO: 1" include the following amino acid sequences:

(b) an amino acid sequence as represented by the sequence corresponding to 35th to 255th amino acid in SEQ ID NO: 1, and (c) an amino acid sequence as represented by the sequence corresponding to 79th to 255th amino acid in SEQ ID NO: 1.

The amino acid sequence of (c) above can be obtained by using a DNA corresponding to the nucleotide sequence of 235th to 765th nucleotides of SEQ ID NO: 2, and the amino acid sequence of (b) above can also be obtained in a similar manner as disclosed in JP-A-2001-46084.

The "DNA that hybridizes with a DNA consisting of a nucleotide sequence coding for the amino acid sequence as set forth in SEQ ID NO: 1 under a stringent condition" refers to a DNA that forms a DNA-DNA hybrid with the DNA consisting of a nucleotide sequence coding for the amino acid sequence as set forth in SEQ ID NO: 1 by hybridization under a high ion concentration [including, for example, 6×SSC (900 mM NaCl, 90 mM sodium citrate), and the like] at a temperature of 65° C., and thus formed hybrid is maintained after being incubated under a condition of a low ion concentration [including for example, 0.1×SSC (15 mM NaCl, 1.5 mM sodium citrate), and the like] at a temperature of 65° C. for 30 minutes, in a Southern hybridization method as described, for example, in "Cloning and Sequence" (directed by Itaru Watanabe; edited by Masahiro Sugiura, 1989, published by Noson Bunkasya), the whole disclosure of which is incorporated herein by reference, and the like.

Examples of the DNA suitably used herein include, for example, a DNA consisting of a nucleotide sequence coding for the amino acid sequence as set forth in SEQ ID NO: 1, and a nucleotide having deletion, substitution or addition of a part of the nucleotide sequence in the nucleotide sequence coding for the amino acid sequence as set forth in SEQ ID NO: 1. Such nucleotides may be produced, for example, by site directed mutagenesis or random mutation to the nucleotide sequence of SEQ ID NO 2 by known manner (W. Kramer, et al Nucleic Acids Research, 1984, vol. 12, pp9441, W. Kramer, H. J. Frits, Methods in Enzymology, 1987, vol. 154, pp.350, or T. A. Kunkel, Proc. of Natl. Acad. Sci. USA, 1985, vol. 82, pp. 488). The nucleotide can be prepared, for example, from *E. coli* JM105/pYHNK2 strain carrying the DNA of SEQ ID NO 2 described below or microorganisms belonging to *Aspergillus flavus* such as ATCC11492.

Examples of the nucleotide sequence coding for the amino acid sequence as set forth in SEQ ID NO: 1 include the nucleotide sequence as set forth in SEQ ID NO: 2.

It is understood that, with reference to the discussion of polynucleotides that hybridise to SEQ ID NO:1, the term "sequence coding for the amino acid sequence" includes the complement of the actual coding sequence.

"Sequence identity of the amino acid with the amino acid sequence as set forth in SEQ ID NO: 1", which may also referred to as homologues of SEQ ID NO:1 are referred to herein. Such homologues typically have at least 60%, preferably at least 70%, 80%, 90%, 95% or 97% homology, for example, over a region of at least 15, 20, 30, 100 more contiguous amino acid of SEQ ID NO:1, and preferably over the region defined by amino acids 35 to 255 or 79 to 255 of SEQ ID NO:1. The homology may be calculated on the basis of amino acid identity (sometimes referred to as "hard homology").

For example, the UWGCG Package provides the BEST-FIT program which can be used to calculate homology (for example used on its default settings)(Devereux et al (1984) Nucleic Acids Research 12, p387–395). The PILEUP and BLAST algorithms can be used to calculate homology or line up sequences (such as identifying equivalent or corresponding sequences (typically on their default settings)), for example as described in Altschul S. F. (1993) J. Mol. Evol. 36:290–300; Altschul, S. F et al (1990) J. Mol. Biol. 215: 403-10.

Software for performing BLAST analyses is publicly available through the National Center for Biotechnology Information (http://www.ncbi.nim.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighborhood word score threshold (Altschul et al, supara). These initial neighborhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) Proc. Natl. Acad.Sci.USA 89:10915–10919) alignments (B) of 50, expectation(E) of 10, M=5, N=4, and a comparison of both strands.

The BLAST algorithm performs a statistical analysis of the similarity between two sequences; see e.g., Karlin and Altschul (1993) Proc. Natl. Acad. Sci. USA 90:5873–5787. One measure of similarity provided by the BLAST algorithm is the smallest sum probability(P(N)), which provides an indication of the probability by which a match between two amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The homologous sequence typically differs from SEQ ID NO: 1 (or any of the regions of SEQ ID NO:1 mentioned above) by less than 5, less than 10, less than 20, less than 50 or less than 100 mutations (each of which may be a substitution, deletion or insertion). These mutations may be measured across any of the regions mentioned above in relation to calculating homology. The substitutions are preferably conservative substitutions. These are defined according to the following Table. Amino acids in the same block in the second column and preferably in the same line in the third column may be substituted for each other:

| ALIPHATIC | Non-polar | GAP |
| --- | --- | --- |
|  |  | ILV |
|  | Polar-uncharged | CSTM |
|  |  | NQ |
|  | Polar-charged | DE |
|  |  | KR |
| AROMATIC |  | HFWY |

Such amino acid sequence can be obtained by using a microorganism (e.g. *E.coli*) transformed with a vector carrying the DNA, or suitable addition of amino acids to the amino acid sequence as defined under (c) above.

The protein of the present enzyme (hereinafter referred to as "the present protein") can be obtained, for example, by a method as disclosed in JP-A-2001-46084.

The protein of the invention may be in the form of a fusion protein, which comprises a sequence corresponding to any of the portions/homologues of SEQ ID No: 1 mentioned herein and other sequences.

The styrene-divinylbenzene copolymer having fine pores with average radius of 200–500 Å (hereinafter referred to as "the present immobilization carrier") is usually used in the form of particles. Examples of the styrene-divinylbenzene copolymer include, for example, a styrene-divinylbenzene copolymer comprising 30% styrene and 70% divinylbenzene and having fine pores with average radius of 200–500 Å.

The specific surface area of the present immobilization carrier is usually 10–1500 m$^2$/g, and the volume of the pores is usually 0.1–3 ml/g. A specific example thereof includes "Diaion HP20SS", trade name under Mitsubishi Chemical Corporation.

In view of the efficiency of the reaction, the polymer particles having small radius are preferably used. Specifically, those having average particle radius of 50–200 µm, and those containing 60% or more particles having a particle radius of 60–110 µm in a particle size distribution are preferred. A specific example of the present carrier of which particles having such a suitable radius includes "Diaion HP20SS", trade name under Mitsubishi Chemical Corporation.

The enzyme preparation of the present invention can be usually produced by bringing the present protein in contact with the present carrier. The process of contacting the present protein with the carrier is usually conducted by adding the carrier to a solution containing the present protein and the resulting mixture is stirred.

The protein as applied above can be used in the form of a purified protein, a crude protein or the like.

The present protein or its solution can be obtained, for example, by known procedures as disclosed in JP-A-2001-46084. Specifically, it can be obtained through culturing e.g., E. coli JM105/pYHNK2 strain carrying the DNA of SEQ ID NO 2 prepared from ATCC11492 by known manners such as cDNA preparation according to a protocol of Bio-sogo catalogue 1997/98 Vol. 1, E-24-27, identifying the desired enzyme activity, primer preparation, PCR reaction using the same.

The obtained protein can be purified by known purification procedures. For example, suitable microbial culture cells are disrupted. This process for the disruption may be conducted by, for example, collecting the microbial cells by e.g., centrifugation from the culture of the microorganism, followed by physical disruption process of the microbial cells such as a ultrasonic treatment; addition of lower alcohol such as ethanol to the culture of the microorganism and settled a while; or the like. Thus resulting disruption solution is subjected to centrifugation, filtration with a membrane filter or the like to eliminate insoluble substances, and thus a clear solution containing the present protein can be prepared.

In addition, the present protein can also be further purified by fractionating thus obtained clear solution optionally utilizing a separation/purification technique such as cation exchange chromatography, anion exchange chromatography, chromatography, gel chromatography.

The temperature employed when the present protein is brought in contact with the present carrier is usually in the range of 1–37° C., and preferably in the range of 5–15° C. The time period for the contact is usually in the range of 1–48 hours. When they are brought in contact, the pH may be usually 4–10, and preferably in the range of 6–8.

The amount of the carrier is usually in the range of 0.01–1 g, and preferably in the range of 0.08–0.12 g per 1000 U (1 U means the amount of the present protein which can hydrolyze racemic N-benzylazetidine-2-carboxylic acid ethyl ester to produce 1 µmol of N-benzylazetidine-2-carboxylic acid in 1 minute) of the present protein.

The activity of the present enzyme can be determined, for example, by preparing a reaction solution by adding 0.02 g of racemic N-benzylazetidinecarboxylic acid ethyl ester and 1.0 ml of methyl t-butyl ether to 3.5 ml of a 100 mM potassium phosphate buffer (pH 7.0) containing a protein; shaking this reaction solution at about 30 to 35° C. for 1 to 24 hours; and thereafter analyzing the amount of (S) form of N-benzylazetidine-2-carboxylic acid present in an aqueous layer obtained by centrifuging the reaction mixture thus obtained.

Immobilization of the present protein onto the carrier can be monitored by, for example, tracing the activity of the solution containing the present protein to hydrolyze racemic N-benzylazetidine-2-carboxylic acid ethyl ester.

The immobilized enzyme of the present invention produced as described above can be isolated by filtration, centrifugation or the like.

Next, the process for the production of the present invention is explained below.

The reaction of the present invention is usually conducted by subjecting a racemic N-substituted cyclic imino ester of formula (1) to a reaction with the enzyme preparation, or the immobilized enzyme of the present invention.

The reaction is usually conducted in the presence of water. Water may be an aqueous buffer solution.

The amount of water is usually 0.5 mol or more per 1 mol of the N-substituted cyclic imino ester compound of formula (1). Water can be also used as a solvent.

Further, organic solvents such as hydrophobic organic solvents, hydrophilic organic solvents or the like may be concomitantly present in the reaction in addition to water. Examples of hydrophobic organic solvent include ethers such as t-butyl methyl ether and isopropyl ether; and hydrocarbons such as toluene, hexane, cyclohexane, heptane and isooctane. Examples of hydrophilic organic solvent include alcohols such as methanol, ethanol, 2-propanol and 1,1-dimethylethanol; ketones such as acetone; nitriles such as acetonitrile. These hydrophobic organic solvent and hydrophilic organic solvent can be used alone or in combination of two or more of them. The hydrophobic organic solvent, hydrophilic organic solvent and the mixture thereof can be also used.

When an organic solvent is used, the amount thereof used is usually 100 parts by weight or less, preferably in the range of 0.1–50 parts by weight per 1 part by weight of the N-substituted cyclic imino ester compound of formula (1).

The reaction is usually carried out through stirring, shaking or the like in such a way where the N-substituted cyclic imino ester compound of formula (1), the immobilized enzyme of the present invention, and additionally organic solvent or the like are mixed as needed.

The pH of reaction mixture is suitably set, typically in the range of pH 4–10, and preferably in the range of pH 6–8 taking account of the initial velocity of the reaction. The reaction temperature is usually in the range of 0–70° C., and preferably in the range of 0–40° C. in light of stability and the initial velocity of the reaction.

Although the amount of the enzyme preparation in the reaction can be suitably set depending on the catalytic activity of the enzyme preparation (immobilized enzyme), it is usually in the ratio of 0.001–0.1 parts by weight per 1 part by weight of the N-substituted cyclic imino ester compound of formula (1).

End point of the reaction can be determined by, for examples tracing the conversion ratio of the N-substituted cyclic imino ester compound of formula (1) in a reaction mixture with liquid chromatography or the like. The reaction is typically terminated at a point where the conversion ratio of the N-substituted cyclic imino ester compound of formula (1) does not exceed 50% in light of the selectivity of the reaction. The reaction time is usually in the range of from about 5 minutes to about 4 days.

After completion of the reaction, the (S)-N-substituted cyclic imino acid of formula (2) can be isolated through, for example, filtrating the reaction mixture, followed by phase separation of an aqueous filtrate and an organic phase (hexane, heptane, t-butyl methyl ether, ethyl acetate, toluene or the like) to remove the unreacted starting compound, applying the aqueous layer to ion chromatography as needed to eliminate salts, followed by concentration. Additionally, the product can be purified by column chromatography or the like as needed.

EXAMPLES

The present invention is explained in more detail below by way of Examples, however, the present invention is not be construed to limit the invention thereto.

Example 1

Water-washed Diaion HP20SS (trade name under Mitsubishi Chemical Corporation), a product which was manufactured by mixing 12 g of Diaion HP20SS and 300 ml of water, followed by stirring for 30 minutes, filtration and additional wash with 400 ml of water, was mixed with 600 g of a clear solution of the protein that was produced as below. The mixture was stirred at 10° C. for 18 hours. Thereafter, the mixture was filtrated, washed with 400 g of water to give the immobilized enzyme of 12.5 g.

To 3.5 ml of 100 mM monopotassium hydrogenphosphate-dipotassium phosphate buffer (pH 7.0), were added 50 mg of the above-described immobilized enzyme and 1.0 ml of t-butylmethyl ether, and the mixture was incubated at 35° C. for 15 minutes. Thereto was added 0.02 g of N-benzylazetidine-2-carboxylic acid ethyl ester, followed by reciprocal shaking (120 str/min) at 35° C. for 16 minutes. Thereafter, 400 µl of this reaction mixture was added to 1 ml of t-butylmethyl ether, and the mixture was centrifuged at 12000 rpm for 5 minutes. Two hundred µl of thus resulting aqueous layer was dissolved in 20 mM monopotassium hydrogenphosphate/acetonitrile: 90/10, and the solution was filtered through a 0.2 µm filter. The filtrate was applied on high performance liquid chromatography. Accordingly, it was confirmed by detecting (S)-N-benzylazetidine-2-carboxylic acid that thus obtained immobilized enzyme had a desired activity.

Example 2

To 77 g of water were added 0.5 g of the immobilized enzyme produced in Example 1 above and 65 g of ethyl N-benzylazetidine-2-carboxylate, followed by stirring at 10° C. for 10 hours. To the reaction mixture, were added 65 g of methylisobutyl ketone and 36 g of ethanol, and further stirring was conducted for 30 minutes. The reaction mixture was thereafter filtrated, and the filtrate was subjected to separation. To the aqueous layer were added 65 g of methylisobutyl ketone and 6.5 g of ethanol followed by stirring for 30 minutes and the separation. This operation was repeated twice. Thus resulting aqueous layer was concentrated under a reduced pressure (10 kPa or lower) to give 60 g of crude (S)-N-benzylazetidine-2-carboxylic acid (43 weight %).

Condition for analysis of N-benzylazetidine-2-carboxylic acid

High Performance Liquid Chromatography column: ODS-A212 (manufactured by Sumika Analysis Center Co., Ltd.)

mobile phase; 20 mM monopotassium hydrogenphosphate/acetonitrile: 90/10 flow rate: 1 ml/min column temperature: 40° C.

detector: UV (220 nm)

retention time of N-benzylazetidine-2-carboxylic acid: 5.5 min

Preparation of Clear Solution of the Present Enzyme

To 10 ml of a sterilized medium (prepared by dissolving 5 g of glycerol, 6 g of yeast extract, 4 g of monopotassium hydrogenphosphate, 9.3 g of dipotassium phosphate in 1000 ml of water) were added 10 µl of a 50 mg/ml aqueous ampicillin solution and 0.1 ml of a glycerol stock of *E. coli* JM105/pYHNK2 strain (see, JP-A-2001-46084). The mixture was then shaken at 30° C. for 9 hours. Thus resulting culture fluid is noted as "culture fluid A".

To 15000 ml of sterilized liquid medium (prepared by dissolving 225 g of glycerol, 150 g of yeast extract, 225 g of multi-amino acids F, 60 g of monopotassium hydrogenphosphate, 36 g of magnesium sulfate, 0.6 g of ferrous sulfate heptahydrate and calcium chloride dehydrate in 13000 ml of water, and further adding water to make the total volume of 150000 ml) were added a 4 M aqueous phosphoric acid solution and 14 w/w % aqueous ammonia to adjust the pH of 7.0. Thereto was added 7.5 ml of the above-described culture fluid A, and aerobic culture with stirring was conducted at 30° C. After 14 hours elapsed from the beginning of the culture, sterilized liquid medium (prepared by dissolving 280 g of yeast extract and 420 g of multi-amino acids F in a mixture of 1100 g of water and 1500 g of glycerol) was gradually added. Furthermore, isopropyl thio β-D-galactoside was added to give 50 µM at 18 hours since the beginning of the culture.

At 40 hours since the beginning of the culture, 1950 ml of ethanol was added to the culture fluid followed by further stirring at 30° C. for 24 hours. Thereafter, 6000 g of this mixture was retrieved, and mixed with 6200 g of water. The solution was subjected to continuous centrifugation treatment (20000 rpm, flow rate: 130 g/min) to give a centrifugation supernatant of 11200 g. To this centrifugation supernatant was added 220 g of Radiolyte #200 (trade name under Showa Chemical Industry Co., Ltd.), followed by stirring. The solution was further filtrated through Radiolyte #200 to give the clear solution of the present protein.

The immobilized enzyme of the present invention enables the production of (S)-N-substituted cyclic imino acids of formula (2) in an efficient manner on a large scale.

What is claimed is:

1. An enzyme preparation comprising:
   (i) a styrene-divinylbenzene copolymer having fine pores with an average radius of 200–500 Å,
   (ii) an enzyme capable of asymmetrically hydrolyzing N-substituted C3–C4 cyclic imino-2-carboxylic acid ester to preferentially produce an (S)-N-substituted C3–C4 cyclic imino-2-carboxylic acid, and
   wherein said enzyme comprises any one of the following amino acid sequences (a) to (f):
   (a) an amino acid sequence as set forth in SEQ ID NO: 1;
   (b) an amino acid sequence as represented by the sequence corresponding to 35th to 255th amino acid in SEQ ID NO: 1;
   (c) an amino acid sequence as represented by the sequence corresponding to 79th to 255th amino acid in SEQ ID NO: 1;
   (d) an amino acid sequence encoded by a DNA, wherein 1) said DNA is a DNA that hybridizes with a DNA consisting of a nucleotide sequence coding for the amino acid sequence as set forth in SEQ ID NO: 1 at a high ion concentration of 6×SSC (900 mM NaCl, 90 mM sodium citrate) at a temperature of 65° C., and 2) the resulting hybrid is maintained after being incubated under a low ion concentration of 0.1×SSC (15 mM NaCl, 1.5 mM sodium citrate) at a temperature of 65° C. for 30 minutes;
   (e) an amino acid sequence that has sequence identity with the amino acid sequence as set forth in SEQ ID NO: 1 of 70% or greater; or
   (f) an amino acid sequence encoded by a nucleotide sequence having the restriction sites as shown in FIG. 1.

2. An enzyme preparation according to claim 1, wherein said enzyme is immobilized onto the copolymer.

3. An enzyme preparation according to claim 1 or 2, wherein the copolymer is a copolymer comprising 30% styrene and 70% divinylbenzene.

4. An enzyme preparation according to claim 3, wherein the copolymer has specific surface area of 10–1500 m²/g, and the volume of the pores is 0.1–3 ml/g.

5. An enzyme preparation according to claim 1, wherein the N-substituted C3–C4 cyclic imino-2-carboxylic acid ester is N-substituted cyclic imino ester of formula (1):

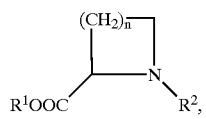
(1)

wherein $R^1$ represents
an alkyl group having 1 to 8 carbon atoms,
an aralkyl group having 7 to 19 carbon atoms,
an alkenyl group having 2 to 5 carbon atoms or
an aryl group having 6 to 12 carbon atoms,
and wherein said alkyl group may be substituted with at least one group selected from an alkoxy group having 1 to 8 carbon atoms, a halogen atom and a nitro group, and
wherein said aralkyl group or aryl group may be substituted on the aromatic ring thereof with at least one group selected from an alkyl group having 1 to 8 carbon atoms, an alkoxy group having 1 to 8 carbon atoms, a halogen atom and a nitro group; and
$R^2$ represents
an aralkyl group having 7 to 19 carbon atoms,
an alkylcarbonyl group having 2 to 5 carbon atoms,
an arylcarbonyl group having 7 to 13 carbon atoms,
an alkyloxycarbonyl group having 2 to 9 carbon atoms,
an aralkyloxycarbonyl group having 8 to 10 carbon atoms,
an alkenyloxycarbonyl group having 4 to 9 carbon atoms,
an aryloxycarbonyl group having 7 to 13 carbon atoms,
an alkyl group having 1 to 8 carbon atoms,
an alkenyl group having 2 to 8 carbon atoms,
an aryl group having 6 to 12 carbon atoms or
an arylsulfonyl group having 6 to 12 carbon atoms,
and wherein said aralkyl group, arylcarbonyl group, aralkyloxycarbonyl group, aryloxycarbonyl group, aryl group or arylsulfonyl group may be substituted at one or more hydrogen atoms bound to the aromatic ring thereof with at least one selected from an alkyl group having 1 to 8 carbon atoms, an alkoxy group having 1 to 8 carbon atoms, a halogen atom and a nitro group, and
wherein said alkylcarbonyl, alkyloxycarbonyl or alkyl group may be substituted with at least one group selected from an alkoxy group having 1 to 8 carbon atoms, a halogen atom and a nitro group; and
n represents 1 or 2.

6. An enzyme preparation according to claim 5, wherein $R^1$ represents a C1–C4 alkyl group, and $R^2$ represents a benzyl group.

7. An enzyme preparation according to claim 6, wherein $R^1$ represents a methyl or ethyl group, $R^2$ represents a benzyl group and n is 1.

8. A process for producing an (S)-N-substituted cyclic imino acid of formula (2):

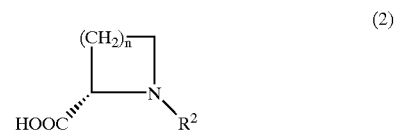
(2)

wherein $R^2$ represents
an aralkyl group having 7 to 19 carbon atoms,
an alkylcarbonyl group having 2 to 5 carbon atoms,
an arylcarbonyl group having 7 to 13 carbon atoms,
an alkyloxycarbonyl group having 2 to 9 carbon atoms,
an aralkyloxycarbonyl group having 8 to 10 carbon atoms,
an alkenyloxycarbonyl group having 4 to 9 carbon atoms,
an aryloxycarbonyl group having 7 to 13 carbon atoms,
an alkyl group having 1 to 8 carbon atoms,
an alkenyl group having 2 to 8 carbon atoms,
an aryl group having 6 to 12 carbon atoms or
an arylsulfonyl group having 6 to 12 carbon atoms,
and wherein said aralkyl group, arylcarbonyl group, aralkyloxycarbonyl group, aryloxycarbonyl group, aryl group or arylsulfonyl group may be substituted at one or more hydrogen atoms bound to the aromatic ring thereof with at least one selected from an alkyl group having 1 to 8 carbon atoms, an alkoxy group having 1 to 8 carbon atoms, a halogen atom and a nitro group, and
wherein said alkylcarbonyl, alkyloxycarbonyl or alkyl group may be substituted with at least one group selected from an alkoxy group having 1 to 8 carbon atoms, a halogen atom and a nitro group; and
n represents 1 or 2,
which process comprises subjecting an N-substituted cyclic imino-2-carboxylic acid ester of formula (1):

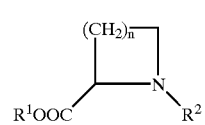
(1)

to a reaction with the enzyme preparation of claim 1, 2, or 3, wherein $R^1$ represents
an alkyl group having 1 to 8 carbon atoms,
an aralkyl group having 7 to 19 carbon atoms,
an alkenyl group having 2 to 5 carbon atoms or
an aryl group having 6 to 12 carbon atoms,
and wherein said alkyl group may be substituted with at least one group selected from an alkoxy group having 1 to 8 carbon atoms, a halogen atom and a nitro group, and
wherein said aralkyl group or aryl group may be substituted on the aromatic ring thereof with at least one group selected from an alkyl group having 1 to 8 carbon atoms, an alkoxy group having 1 to 8 carbon atoms, a halogen atom and a nitro group; and
$R^2$ and n have the same meaning as defined above.

9. A process according to claim 8, wherein $R^1$ represents a C1–C4 alkyl group, and $R^2$ represents a benzyl group.

10. A process according to claim 9, wherein $R^1$ represents a methyl or ethyl group, and $R^2$ represents a benzyl group, and n is 1.

* * * * *